United States Patent [19]

Ross, Jr. et al.

[11] Patent Number: 4,672,042
[45] Date of Patent: Jun. 9, 1987

[54] METHOD OF AND APPARATUS FOR CHROMATOGRAPHIC ANALYSIS

[75] Inventors: James W. Ross, Jr., Cambridge, Mass.; Lionel S. Goldring, Woodbridge, Conn.; John H. Riseman, Cambridge, Mass.

[73] Assignee: Orion Research Puerto Rico, Inc., Rio Piedras, P.R.

[21] Appl. No.: 686,299

[22] Filed: Dec. 26, 1984

Related U.S. Application Data

[63] Continuation of Ser. No. 332,370, Dec. 21, 1981, abandoned.

[51] Int. Cl.$^4$ .................. G01N 30/14; G01N 30/96; B01D 13/00
[52] U.S. Cl. .................. 436/161; 73/61.1 C; 210/198.2; 210/321.1; 210/649; 210/656; 422/61; 422/70; 436/150; 436/175; 436/178
[58] Field of Search .................. 422/70, 89, 68, 69, 422/61; 436/161, 178, 150, 175, 176, 177; 55/67, 16, 158, 386, 197; 210/500.2, 321.2, 198.2, 656, 651, 659, 638, 649, 321.1; 73/61.1 C

[56] References Cited

U.S. PATENT DOCUMENTS

| | | | |
|---|---|---|---|
| 3,450,508 | 6/1969 | Cooper et al. | 210/321.2 X |
| 3,495,943 | 2/1970 | Kapff | 436/178 X |
| 3,751,879 | 8/1973 | Allington | 55/158 |
| 3,757,947 | 9/1973 | Wakefield et al. | 210/321.2 X |
| 4,056,587 | 11/1977 | Honkanen et al. | 264/53 |
| 4,131,428 | 12/1978 | Diggens | 436/178 X |
| 4,272,246 | 6/1981 | Fritz et al. | 436/119 X |
| 4,448,691 | 5/1984 | Davis | 210/656 |
| 4,451,374 | 5/1984 | Peterson et al. | 210/656 |
| 4,474,664 | 10/1984 | Stevens et al. | 436/150 X |

*Primary Examiner*—Michael S. Marcus
*Assistant Examiner*—Robert J. Hill, Jr.
*Attorney, Agent, or Firm*—Cesari & McKenna

[57] ABSTRACT

An ion-chromatography system for analyzing one or more ionic species of a given polarity in solution, the system comprising an ion-exchange material reactive with such species, an eluant fluid, means for adding the eluant fluid and ionic species to the separation column, a stripper column and a detector. The eluant fluid includes at least a pair of electrically neutral molecular species reactive with one another to provide ionic constituents, the molecular species being in substantial equilibrium with the ionic constituents. The stripper column is positioned at the outlet of the separation column to receive the eluant fluid from the latter and reduce the concentration of the ionic constituents in the eluant fluid. The stripper column includes a conduit relatively permeable to the neutral molecular species in the eluant and relatively impermeable to the ionic constituents. Means are also provided for removing any of the neutral species that permeate the conduit, whereby a concentration gradient is established across the conduit. The detector is provided to quantitatively measure the chromatographically separated ionic species in the eluant discharged from the stripper column.

27 Claims, 4 Drawing Figures

U.S. Patent  Jun. 9, 1987  4,672,042
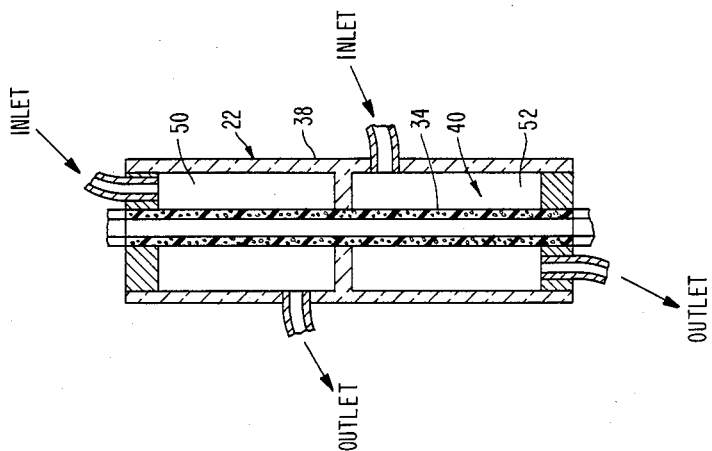
FIG. 4
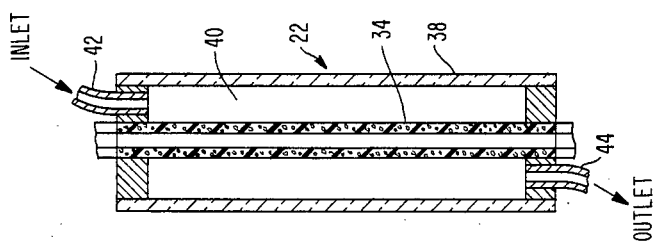
FIG. 3
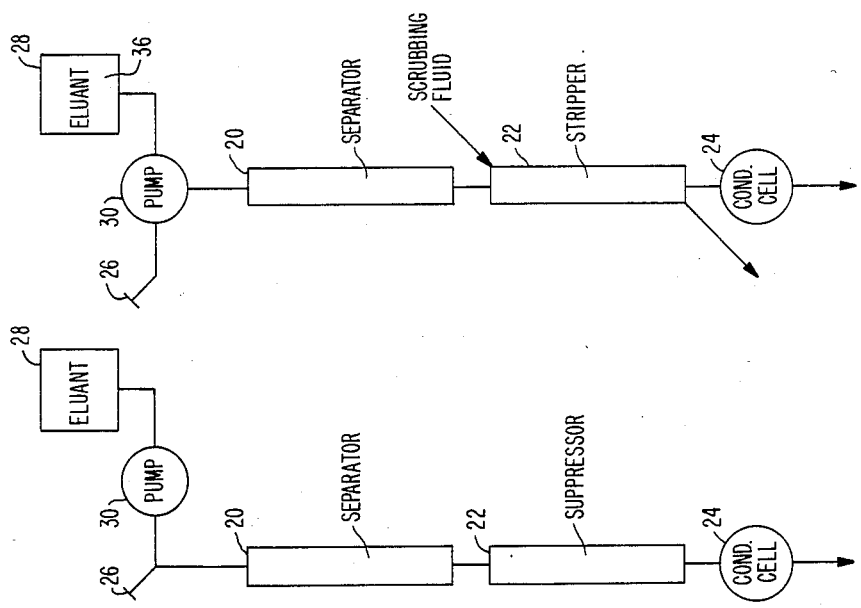
FIG. 2
FIG. 1 (PRIOR ART)

METHOD OF AND APPARATUS FOR CHROMATOGRAPHIC ANALYSIS

This is a continuation of application Ser. No. 332,370, filed Dec. 21, 1981, now abandoned.

FIELD OF THE INVENTION

This invention relates to an improved ion chromatography system and particularly to apparatus and methods for chromatographic separation and analysis of a mixture of ionic species in a test sample.

PRIOR ART

Generally, ion-exchange chromatography involves the binding of the ionic species in a test solution to a stationary pahse preferably formed as a column or bed of solid material such as a resin having fixed ionic groups (such as $SO_3^-$) along with counter-ions of opposite charge (e.g., $Na^+$), and the subsequent passage of a mobile phase or liquid eluant through that stationary phase to effect separation of the ionic species from the stationary phase. The counter-ions are also normally present in the mobile phase in the form of a salt (e.g. NaCl). Ionic sample molecules (e.g., $X^+$), are retained by the stationary phase through ion-exchange, as for example:

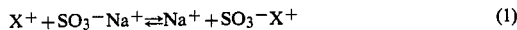

$$X^+ + SO_3^- Na^+ \rightleftharpoons Na^+ + SO_3^- X^+ \qquad (1)$$

Sample ions that interact weakly with the ion exchanger in the presence of competing mobile ions will be retained weakly on the column and can be eluted earlier from the ion-echanger through the use of an appropriate reagent or eluant fluid to form a chromatogram—a train or bands of ionic constituents in the column effluent. Sample ions interacting strongly with the ion-exchanger phase will elute later. The effluent from the ion-exchanger column is then examined by a detector to determine the time sequence in which the various separated groups of ions are eluted from the ion-exchanger. Such detection is achieved through a number of different type of detectors such as colorimeters, amperometric detectors, refractive index detectors, UV absorption detectors and fluorescence detectors to name but a few.

In ion-exchange separation, the solid phase or column is usually a packed bed of bonded-phase ion exchanger in finely comminuted form. As known, it must first be determined whether an anion or cation exchanger is appropriate as the solid phase for the sample of interest. The mobile phase is a solvent such a water with one or more additives such as buffers, neutral salts or organic solvents.

Because the analysis of some species has been limited by the lack of a suitable detector, it has been suggested that a conductivity detector be used for monitoring the ionic species of interest in the column effluent. Conductivity is the universal property of ionic species in solution and shows a simple dependence on the concentration of that species. However, in ion-exchange separation, the conductivity response of the eluted ionic species in the sample is swamped by the conductivity of the ion concentration of the electrolyte comprising part of the eluant. Small et al (Anal. Chem. 47 1801 (1975)) solved this problem by adding a second ion-exchanger column to reduce the background electrolyte after separation had been effected in the first column. By suppressing the effect of the ionic constituents in the eluant during the measurement of conductivity, the ionic species of interest is left as the major conductive component in the column effluent. This technique has become known simply as ion-chromatography as distinguished from ion-exchange chromatography. The technique of Small et al, and the suppressor column apparatus for carrying out various aspects of ion-chromatography are described in detail in U.S. Pat. Nos. 3,897,213; 3,915,642; 3,918,906; 3,920,398; 3,923,460; 3,925,019; and 3,966,596.

Ion-chromatography in accordance with the above patents, while permitting the use of conductivity detectors, is nevertheless limited in that the conductivity of the eluant fluid from the exchanger column in many instances may not be completely suppressed. For example, where the eluant contains an alkaline metal bicarbonate, a cationic suppresor column will purportedly remove the bicarbonate ions by forming $H_2CO_3$ which is neutral electrically. Therefore $H_2CO_3$ should not per se contribute to conductivity. However, in this respect the effluant is essentially the same as water saturated with $CO_2$ and therefore will exhibit a conductivity of about 20 to 40 $\mu$mhos. This latter value is to be compared to the conductivity of, for example, pure distilled water which is about 0.04 $\mu$mhos. In other words, although a neutral molecule has been formed from the ionic constituents, it may still provide a large electrically conductive background which limits the signal-to-noise ratio obtainable in ion-chromatography.

Also, in ion-exchange chromatography the ion-exchanging suppressor column must be periodically regenerated. This is a time-consuming procedure, and during the time that the stripper column is being regenerated, the apparatus of is not available for use. The minimize the frequency of regeneration, the volume ratios of the suppressor column with respect to the separator column should be kept as low as possible, typically at a ratio of 1:1. This unfortunately, essentially doubles the cost of the ion-exchange materials required.

A principal object of the present invention is to overcome these problems in the prior art by providing an ion-chromatography system which minimizes the background conductivity of the eluant fluid.

Another object of the present invention is to provide an ion-chromatography system which omits a second ion exchange resin column or bed which has heretofore been employed in ion-chromotography to suppress the background conductivity of the eluting fluid, and to provide an alternative system for reducing the background electrical conductivity.

SUMMARY OF THE INVENTION

To effect these objects, the present invention provides a novel ion-chromotography system for analyzing one or more ionic species of a given polarity in solution. The system employs an ion-exchange resin column or bed reactive with such ionic species, and an eluant fluid capable of eluting the ionic species of interest from the ion-exchange resin. The eluant fluid includes at least a pair of electrically neutral molecular species reactive with one another to form ionic constitutents, the neutral molecular species being in substantial equilibrium with the ionic constitutents. The invention also includes a stripper column positioned at the outlet of the ion-exchange resin separation column for reducing the ionic conductivity of the eluant fluid discharged from the separation column. The stripper column comprises a conduit which receives the eluant fluid from the ion-exchange resin separation column, at least a portion of the conduit wall being relatively permeable to the neutral molecular species in the eluant fluid and relatively impermeable to the ionic species of interest and the ionic constituents in the eluant.

In carrying out the method of the present invention, a solution containing one or more ionic species of interest having one polarity is added to an ion-exchange separation column containing an ion-exchange material, such as a resin. Such material is capable of retaining the ionic species and of subsequently releasing those ionic species into the eluant fluid to provide a chromatographic separation. The eluant fluid contains a pair of neutral molecular species reactive with one another to form ionic constituents. The ionic constituents must be of sufficient concentration to provide the competitive background which effects the separation of the ionic species of interest from the ion exchange material. The concentration of the ionic constituents in the eluant fluid provides the mechanism for separating the ionic species of interest from the ion-exchange material. The effluent from the ion-exchange column containing the ionic species of interest is passed through a stripper column, at least a portion of the wall of which is permeable to the neutral molecular species in the fluid. By permeating through wall of the stripper column, the neutral molecules become removed from the fluid without materially affecting the chromatographic separation. The eluant from the stripper column is then passed through a detector capable of quantitatively measuring the chromatographically separated ionic species by electrical conductivity or similar detection means.

Yet other objects of the present invention will in part be obvious and will in part appear hereinafter. The invention accordingly comprises the apparatus possessing construction, combination of elements and arrangement of parts, and the method comprising the several steps and relation of one or more of such steps with respect to each of the others, all of which are exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein;

FIG. 1 is a schematic representation of a prior art ionchromatography system;

FIG. 2 is a schematic representation of an embodiment of the apparatus of the present invention;

FIG. 3 is a schematic cross-section taken through a stripper column of the apparatus of FIG. 2; and FIG. 4 is a schematic cross-section taken through an alternative form of a stripper column of the present invention.

Referring now to FIG. 1 of the drawings, a prior art apparatus is seen to comprise first chromatographic column 20 arranged in flow sequence with second chromatographic or suppressor column 22 connected to the outlet of first column 20, and conductivity cell 24 connected to the outlet of second or suppressor column 22. As well known in the art, columns 20 and 22 are conduits or tubes ordinarily formed of material, typically glass, stainless steel or the like, chemically inert to the ionic species of interest and to the eluant fluid. These columns usually have comparatively small internal diameters of a few millimeters, and are filled with appropriate ion exchangers. Means, such as inlet 26, are provided for introducing into column 20, a sample solution containing a plurality of ionic species of like polarity, which species are to be chromatographically separated. The system also includes source 28 of eluant fluid and typically pump 30 for supplying to inlet 26 of column 20 a stream of eluant at a predetermined rate with which to elute the ionic species of interest from the ion-exchange material in separator column 20.

As well known, for separation of a plurality of anions introduced at 26, separator column 20 preferably is packed with an anion separator resin in the form of particles or beads in the range of about 200 to 400 mesh, the resin being typically a surface sulfonated styrene-divinyldenzene copolymer coated with fine particles of a strong base anion exchanger resin. The eluant fluid in source 28 is typically an aqueous solution containing $NaHCO_3$ and $Na_2CO_3$. The sample ions ($BR^-$, $Cl^-$, $F^-$, $NO_3^-$, $SO_4^{-2}$ etc) introduced into column 20, bind to the resin in the separator column. When eluted, the ionic spceies are chromatographically segregated into distinct bands within the eluant fluid flowing through separator column 20. The residence time for each anionic species is a function of the affinity of that species to the ion-exchange resin in the column, the nature of the eluant, the length of column 20, and the flow rate of the eluant stream as determined by pump 30.

The eluant fluid discharged from column 20 is then received by suppressor column 22. The latter is similar to separator column 20 except that the ion-exchanger resin used in the suppressor column is a high capacity resin which can react with relatively large volumes of eluant without allowing highly ionized background-molecules in the fluid to reach conductivity cell 24. The resin in column 20 is typically a polystyrene or modified polystyrene copolymer cross-linked with divinylbenzene and bearing nuclear groups which act as acid exchange sites. Where the ion sample introduced at inlet 26 for separation is anionic, the resin in column 21 is typically a strong acid resin in hydrogen form. In such case, the strong acid resin removes $Na^+$ and protonates the $HCO_3^-/CO_3^{2-}$ to $H_2CO_3$. By this mechanism all of the anionic species exit from the suppressor column in acid form while the cations in the test sample are also exchanged for $H^+$ within the suppressor column. The individual bands of separated anions are detected directly by conductivity measurement in cell 24, the eluant suppression system provided by suppresor column 22 having substantially reduced the electrical background provided by the $NaHCO_3/Na_2CO_3$ in the eluant previously.

The system of the present invention as shown schematically in FIG. 2 may superficially resemble that of FIG. 1, but differs in a substantial and significant manner. The system of FIG. 2 includes sample injection at point 26, eluant source 28, eluant pump 30 and separator column 20, all of which can be the same as that shown in FIG. 1. However, the reduction of the ionic background in the eluant fluid in the embodiment of FIG. 2 is accomplished through substantially different means than that of FIG. 1. As shown particularly in FIG. 3, stripper column 22 includes at least one internal conduit 34 the inlet to which is connected to the outlet from separator column 20. Conduit 34 contains no resins or ion exchange-separator bed, but is simply an open channel, tube or conduit having a comparatively small internal diameter e.g. one millimeter or less.

Eluant fluid 36, stored in source 28, contains at least a pair of electrically neutral molecular species which are reactive with one another to provide a compound which dissociates in the solvent to form ionic constitutents. As previously noted, these ionic constituents must be present in sufficient concentration to provide the competitive background which effects the chromatographic separation of the ion species from the ion-exchange material. It is by the dissociation of the compound formed by the reaction of the two neutral molecular species that the necessary ionic constitutents in the eluant fluid are formed and maintained. Within the eluant fluid, therefore, the neutral molecular species remain substantially in equilibrium with the ionic constituents. At the operating temperature of separator column 20, this equilibrium in the eluant fluid must not be so biased toward production of ionic constituents that the neutral molecular species are present only in trace amounts. Preferably, the neutral molecular species should be selected so that for the operating temperature and pressure in conduit 34, the equilibrium within the eluant fluid yields the neutral molecular species in a ratio of not less than 1:5 with respect to the ionic constitutents.

The neutral molecular species reactive with one another in the eluant are present in pairs, one of which includes acids and acid-formers, the other of which includes bases and base-formers. Typically, one can employ neutral acid-formers such as $CO_2$, $SO_2$ and the like, and weak organic acids such as acetic, formic, proprionic acids and the like, all of which are substantially volatile at the operating temperature and pressure in conduit 34. Highly reactive with such acids and acid-formers in aqueous solution, are substantially electrically neutral bases and base-formers such as $NH_3$, amines, pyridine, aniline, picoline and the like, which also exhibit substantial volatility at the operating temperatures and pressures in conduit 34.

Using a $CO_2$/amine pair as exemplary of a typical reactive neutral molecular species useful in the eluant of the present invention, the equilibrium in the eluant can be illustrated by the following equation:

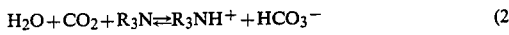

$$H_2O + CO_2 + R_3N \rightleftharpoons R_3NH^+ + HCO_3^- \qquad (2)$$

Unlike column 22 in FIG. 1, the conduit of which serves primarily as an enclosure for ion-exchange material, at least a portion of the wall in conduit 34 in column 22 is formed of material which is permeable to the electrically neutral molecular species in the eluant fluid and is substantially impermeable to both the ion species of interest or the ionic constituents, in the eluant fluid. Such permeability is illustrated by material with a microporous structure, or material in which the neutral molecular species are soluble, or material through which the molecular species can diffuse. As long as the material is permeable to electrically neutral molecules and is impermeable to electrically charged ionic molecules, the specific transport mechanism by which the neutral molecules species in the eluant are transmitted through the conduit is of no consequence, and all such materials are deemed to be within the scope of the present invention.

Typical conduit wall materials are microporous silicon rubber, fluorinated hydrocarbon tubing and the like. Thus, when the eluant enters conduit 34, some of the neutral molecular species in the eluant will initially permeate or diffuse through or into the wall of conduit 34. The removal of the latter molecules from the eluant stream will tend to force the equilibrium, such as is illustrated in Equation 2, to the left and form more electrically neutral molecules in the eluant stream at the expense of the concentration of ionic constitutents. As the eluant flows deeper into conduit 34 and additional neutral molecular species permeate through the conduit wall, the equilibrium concentration continues to shift to the left. Depending upon the residence time of the eluant fluid in conduit 34, the permeability of the wall of conduit 34, and the volatility of the neutral molecular species in the eluant fluid, the leftward shift in the equilibrium equation will continue until the ionic constituents are substantially depleted from the eluant. The residence time of the eluant in conduit 34 necessary to effect removal of sufficient neutral molecules from the eluant to reduce the ionic background to a desired minimum is controlled by such factors as the flow rate provided by pump 30, the internal diameter of conduit 34 and the permeability of the material of conduit 34 to the neutral molecules. Additional external factors controlling or affecting permeability are the temperature of the eluant stream and conduit 34, and the nature of the external environment around conduit 34, i.e., pressure, chemical reactivity and the like.

For efficient permeation of the material forming conduit 34 an active mechanism able to remove the permeated molecules from the conduit exterior is preferred. This will maintain a concentration gradient across the conduit wall and prevent local buildup of molecules leading to stagnation which would prevent continued permeation. Consequently, as shown in FIG. 3, in a preferred embodiment of the invention, conduit 34 is surrounded by jacket 38 spaced therefrom to provide plenum 40 about the exterior of conduit 34. Inlet and outlet means 42 and 44 respectively are provided through jacket 38 to plenum 40 so that a stream of scrubbing or purging fluid can be passed through plenum 40 to scrub out such neutral molecules which have permeated from the interior of conduit 34 to its exterior surface. Such a purging fluid can be an air flow or an inert gas stream, which can be heated above room temperature as desired in order to warm conduit 34 and the eluant passing therethrough. As an example, a steam flow is an inexpensive and readily available scrubbing fluid. The heating of the conduit serves to promote permeation, and in some instances, also encourages additional permeation of water molecules through the permeable wall of conduit 34. In these latter examples, the outward permeation of water vapor serves to increase the relative concentration of the ionic species of interest carried in the eluant stream in conduit 34, thereby increasing the efficiency of the system.

It will be appreciated that conduit 34 need not be a linear element as shown in FIG. 3, but can be disposed in many different configurations such as coils, loops and the like in order to increase the surface area of the permeable material available and to reduce the size of the equipment. Similarly, conduit 34 need not be a single passageway, but can be formed as a plurality of parallel tubes of reduced inner diameter and having a common inlet and a common outlet, thereby substantially increasing the ratio of area of permeable wall per unit volume of eluant and increasing the rate of permeation of the neutral molecular species through the conduit wall.

It will also be appreciated that the purging fluid need be neither a gas nor of an inert nature, but can instead be a liquid reactive with the neutral molecular species which have permeated through the wall of conduit 34. For example where one of the neutral molecular species is $CO_2$, an aqueous NaOH solution in plenum 40 can be used to scrub the $CO_2$ from the plenum by chemical reaction rather than by mechanical action. Because in most instances it would be difficult to find a purging fluid chemically reactive with both neutral molecular species permeating through the wall of conduit 34, it is preferred to use apparatus of the type shown particularly in FIG. 4. The plenum 40 shown therein is divided into two separate chambers 50 and 52, each sealed from one another and having its own inlet and outlet. Thus, chamber 50 can be filled with a fluid reactive with one of the permeated molecular species while chamber 52 can be filled with a second fluid reactive with the other of the permeated neutral species. For example, using the species set forth in equation (2), one of the permeated neutral species is $CO_2$ and the other is an amine ($R_3N$). Chamber 50 would include a basic fluid such as aqueous sodium hydroxide which would react with the $CO_2$ but not with the amine. The reaction of $CO_2$ with the NaOH would continuously deplete the gas at the outer surface of conduit 34 and would maintain a vapor-pressure gradient across the wall of conduit 34 with respect to $CO_2$. This gradient will promote a continued permeation of $CO_2$, but because no like gradient there appears with respect to the amine, permeation of the amine through that portion of the wall of conduit 34 is inhibited and the amine will remain in the eluant stream in conduit 34 until the eluant passes into that section of conduit 34 surround by chamber 52.

Chamber 52 in turn would include a volume of an acid such as 0.1 M $H_2SO_4$, to provide chemical scrubbing of the amine. Amine molecules permeating the wall of conduit 34 into chamber 52, react with the acid and the concentration or vapor-pressure gradient created across the wall of that portion of conduit 34 provides the desired mechanism for removing the amine molecules from the eluant.

The following examples serve to illustrate the invention but are not to be considered limiting in any sense:

EXAMPLE 1

A 0.01 M aqueous solution of pyridinium bicarbonate was prepared by mixing aliquots of pyridine ($C_6H_5N$) and water and bubbling $CO_2$ through the mixture until equilibrium was achieved. The pyridinium bicarbonate solution, having a pH of 5.9, was employed as the eluant for chromatographic separation of anions from an anionic ion-exchanger separator column of the type hereinbefore described. A stripper conduit was provided in the form of an 18′9″ length of microporous silicone rubber tubing having an internal diameter of 0.058″ (1 mm) and an external diameter of 0.077″. The tubing was externally surrounded by a 0.1 M NaOH aqueous solution at 95° C. The eluant was pumped through the system at a flow rate of approximately 1 ml/min.

Conductivity cells were provided at both the inlet and outlet of the stripper column to check the effectiveness of the latter in reducing the background conductivity provided by the eluant. At the stripper column inlet, the background conductivity measured 217 $\mu$mhos and at the stripper column outlet measured 7 $\mu$mhos, indicating that the stripper column had reduced the background conductivity by a factor of 31.

EXAMPLE 2

$CO_2$ was bubbled through a mixture of aliquots of aniline (phenylamine) and water until equilibrium was achieved and the resulting solution of anilinium bicarbonate, adjusted to 0.1 M, was used as an eluant as in Example 1, the tubing being surrounded by the same NaOH scrubbing solution held at 90° C. The background conductivity at the input of the stripper column measured 500 $\mu$mhos, and at the outlet of the stripper column measured 4.5 $\mu$mhos.

EXAMPLE 3

Example 1 was repeated using an eluant of 0.1 M methoxy anilinium bicarbonate (prepared as in Example 2 but using 2, methoxy aniline in place of aniline) provided to the stripper column at a flow rate of 2 ml/min. The background conductivity readings at the inlet and outlet of the stripper column measured 800 $\mu$mhos and 24 $\mu$mhos. When the flow rate was reduced to 1 ml/min, the measured background conductivity at the outlet of the stripper column dropped to 5 $\mu$mhos.

EXAMPLE 4

A 0.1 M aqueous solution of pyridinium bicarbonate, prepared as described in Example 1, was provided as an eluant for chromatographic separation of ions of interest from an anionic-exchange separator column of the type hereinbefore described. A stripper conduit was connected to the output of the separation column, the stripper column including an 18′9″ length of the silicone rubber tubing of Example 1. One half of the length of the tubing was surrounded by a first chamber containing a 0.1 M NaOH solution, the second half of the tubing being surrounded by a second chamber containing 0.25 N HCl, both scrubbing fluids being maintained at 95° C. At an eluant flow rate of 2 ml/min, the background conductivity at the input to the stripper conduit measured 1.12 mmhos, and the background conductivity at the outlet measured 8.1 $\mu$mhos. When the eluant flow rate was reduced to 1 ml/min, measurement of the background conductivity at the stripper column output dropped to 4.3 $\mu$mhos.

EXAMPLE 5

A 0.1M aqueous solution of pyridinium bicarbonate, as in Example 4, was provided as an eluant, but the stripper conduit was externally scrubbed with a flow of steam. The measurement of background conductivity at the stripper column inlet measured 2.6 mmhos and at the oulet measured 0.55 mmhos.

EXAMPLE 6

A 0.1 M phenol-ammonia solution, prepared by mixing appropriate amounts of phenol and ammonium hydroxide, was provided as an eluant for chromatographic separation of ions from an anionic ion exchange separator column. A stripper conduit according to the present invention was provided in the form of about 10′ of tubing of microporous fluorinated hydrocarbon (Goretex brand tubing available from W. L. Gore Associates, Elkton, Md.) with an internal diameter of about 1 mm. Half of the tubing was immersed in an aqueous solution of 0.1 N $H_2SO_4$, the other half of the tubing being immersed in an aqueous solution of 0.1 M $Na_3PO_4$. The background conductivity at the inlet to the stripper column measured 7.6 mmhos and the background conductivity at the outlet from the column measured 0.12 mmhos.

EXAMPLE 7

An eluant solution of 0.1 M 2,4-pentanedione ammonium salt was prepared by mixing aliquots of the amine and ammonium hydroxide. The eluant, with a pH of about 9, was fed into a stripper column of about 5' of the Goretex tubing surrounded by a scrubbing fluid of 0.1 N $H_2SO_4$ at 95° C. The background conductivity at the inlet to the striper column measured 2.19 mmhos and at the outlet of the stripper column measured 1.68 mmhos for an eluant flow rate of 1 to 2 ml/min.

EXAMPLE 8

An eluant solution of 0.01 M picolinium bicarbonate was prepared by mixing aliquots of picoline (methyl pyridine) and water and bubbling $CO_2$ therethough until fully reacted. The eluant, at pH 5.5, was fed to a stripper column of about 10' of the Goretex tubing surrounded by a scrubbing fluid of 0.1 N $H_2SO_4$ at 95° C. The background conductivity at the inlet to the stripper column measured 267 $\mu$mhos and at the outlet of the stripper column as 3 $\mu$mhos for an eluant flow rate of 1 to 2 ml/min.

EXAMPLE 9

Upon repeating Example 8 with, however, a stripper conduit made of about 10' of expanded polypropylene tubing of 1 mm internal diameter, the background conductivity at the inlet to the stripper column measured 230 $\mu$mhos and at the outlet, 2 $\mu$mhos.

EXAMPLE 10

Aliquots of 1,1,1 triflouro-2,4-pentanedione and $NH_4OH$ were mixed to provide a 0.01M solution of eluant at a pH of about 5.5. The latter was fed to a stripper column of about 10' of the Goretex tubing. The background conductivity at the inlet to the stripper column measured 750 mmhos and at the outlet of the stripper column, 440 mmhos, for an eluant flow rate of 2 ml/min.

EXAMPLE 11

Example 6 was repeated using, however, an eluant solution of $6.5 \times 10^{-2}$ M picolinium bicarbonate, and 35' of microporous silicone rubber tubing of 1 mm internal diameter as the stripper conduit. The background conductivity at the stripper inlet read 900 $\mu$mhos and at the outlet of the conduit measured 3 $\mu$mhos. Upon repeating this example but with a reduced length (20') of the tubing, the measurements of background conductivity were 900 $\mu$mhos and 7 $\mu$mhos at the stripper inlet and outlet respectively.

EXAMPLE 12

Example 1 was repeated except that the eluant solution was a 0.05 M solution of picolinium bicarbonate, the stripper column conduit was formed of 6' of expanded polystyrene tubing of 1 mm internal diameter, and the conduit was surrounded by a steam atmosphere. The background conductivity at the stripper conduit inlet measured 1 mmhos and at the outlet, 0.8 $\mu$mhos.

Since certain changes may be made in the above apparatus and method without departing from the scope of the invention involved, it is intended that all matter contained in this above description or shown in the accompanying drawings shall be interpreted as illustrative and not in a limiting sense.

What is claimed is:

1. An ion exchange chromatography apparatus for analysis of a plurality of ionic species of the same polarity in a test sample, said apparatus comprising in combination:

means defining and containing a source of an eluant fluid containing at least two neutral molecular species which are reactive with one another to form ionic constituents, said ionic constituents being in substantial equilibrium with said neutral molecular species;

separation column means containing ion exchange material for chromatographic separation of ionic species in a test sample by ion exchange;

means for adding a test sample to said separation column means;

means for adding said eluant fluid to said separation column means; stripper means for receiving eluant fluid from said separation column means, said stripper means comprising a conduit having an exterior and interior surface, a portion of said conduit being substantially permeable to said neutral molecular species in said eluant fluid and substantially impermeable to said ionic constituents in said eluant fluid; and detector means for receiving eluant fluid from said stripper means and for quantitatively measuring chromatographically separated ionic species present in eluant fluid received from said stripper means.

2. The ion exchange chromatography apparatus according to claim 1 wherein said portion of said conduit is permeable to water vapor.

3. The ion exchange chromatography apparatus according to claim 1 wherein said portion of said conduit comprises microporous silicone rubber.

4. The ion exchange chromatography apparatus according to claim 1 wherein said portion of said conduit comprises expanded polystyrene.

5. The ion exchange chromatography apparatus according to claim 1 wherein said portion of said conduit comprises microporous fluorinated hydrocarbon.

6. The ion exchange chromatography apparatus according to claim 1 including means for controlling flow of said eluant fluid through said apparatus.

7. the ion exchange chromatography apparatus according to claim 1 wherein one of said neutral molecular species is a base.

8. The ion exchange chromatography apparatus according to claim 1 wherein one of said neutral molecular species is a base former.

9. The ion exchange chromatography apparatus according to claim 8 wherein said base former is selected from the group consisting of ammonia, amines, pyridines, anilines and picolines.

10. The ion exchange chromatography apparatus according to claim 1 wherein one of said neutral molecular species is an acid former.

11. The ion exchange chromatography apparatus according to claim 10 wherein said acid former is selected from the group consisting of carbon dioxide and sulfur dioxide.

12. The ion exchange chromatography apparatus according to claim 1 wherein one of said neutral molecular species is an acid.

13. The ion exchange chromatography apparatus according to claim 12 wherein said acid is a weak organic acid.

14. The ion exchange chromatography apparatus according to claim 1 wherein said stripper means further comprises means defining a plenum in contact with the exterior surface of said conduit; and means for introducing a purging fluid into said plenum for removing from said exterior surface such molecules of said neutral molecular species as have permeated said portion of said conduit.

15. The ion exchange chromatography apparatus according to claim 14 wherein said plenum is a single chamber.

16. The ion exchange chromatography apparatus according to claim 14 wherein said plenum includes a plurality of independent chambers.

17. The ion exchange chromatography apparatus according to claim 14 wherein said purging means includes means for introducing a reagent chemically reactive with at least one of said neutral molecular species.

18. The ion exchange chromatography apparatus according to claim 14 wherein said purging means includes means for introducing a basic solution into said plenum.

19. The ion exchange chromatography apparatus according to claim 14 wherein said purging means includes means for introducing an acidic solution into said plenum.

20. The ion exchange chromatography apparatus according to claim 14 wherein said eluant fluid includes said ionic constituents in sufficient concentration to provide competetive background to effect separation of ionic species from said ion exchange material of said separation column means.

21. The ion exchange chromatography apparatus according to claim 14 wherein said purging means comprises means for introducing a purging flow of gas.

22. The ion exchange chromatography apparatus according to claim 21 which includes means for conveying through said purging means a flow at a temperature above ambient room temperature.

23. In an ion-chromatographic method for analysis of a plurality of ionic species of the same polarity in a test sample comprising adding a test sample containing a plurality of ionic species of the same polarity to a separation column means containing ion exchange material, adding an eluant fluid containing ionic constituents to the separation column means to separate the plurality of ionic species in the sample and elute such ionic species from the separation column means in said eluant fluid, passing the eluant fluid containing the separated and eluted ionic species from the separation column means to a stripper means to reduce the concentration of the ionic constituents in the eluant fluid and passing the eluant fluid from the stripper means to a detecting means to detect the plurality of ionic species in the eluant fluid, the improvement wherein said eluant fluid is a solution containing at least two neutral molecular species reactive with one another to form the ionic constituents, said neutral molecular species being in equilibrium with said ionic constituents in said eluant; providing said stripper means with a conduit, a portion of which is substantially permeable to said neutral molecular species and substantially impermeable to said ionic constituents, and wherein said eluant is passed through said conduit at a rate sufficient to permit said neutral molecular species to be separated from said eluant fluid by permeation of said neutral molecular species through said portion of said conduit and drive said equilibrium toward continued formation of said neutral molecular species from said ionic constituents to thereby reduce the concentration of said ionic constituents in said eluant.

24. The method as defined in claim 23 including the step of scrubbing neutral molecular species that permeate said portion of said conduit from said portion with a scrubbing fluid.

25. The method as defined in claim 24 wherein said step of scrubbing is achieved by flowing said scrubbing fluid past said conduit to entrain neutral molecular species that permeate said portion of said conduit.

26. The method as defined in claim 24 including the step of heating said scrubbing fluid sufficiently to raise the temperature of said conduit and eluant fluid contained therein above ambient temperature.

27. The method as defined in claim 24 wherein said step of scrubbing is achieved by chemically reacting neutral molecular species that permeate said portion of said conduit with a suitable reagent.

* * * * *